(12) United States Patent
Smith

(10) Patent No.: US 12,208,207 B2
(45) Date of Patent: Jan. 28, 2025

(54) SELF-RETAINING ORAL DEVICE

(71) Applicant: David Smith, Richmond, IN (US)

(72) Inventor: David Smith, Richmond, IN (US)

( * ) Notice: Subject to any disclaimer, the term of this patent is extended or adjusted under 35 U.S.C. 154(b) by 1163 days.

(21) Appl. No.: 16/849,772

(22) Filed: Apr. 15, 2020

(65) Prior Publication Data

US 2020/0246017 A1 Aug. 6, 2020

Related U.S. Application Data

(63) Continuation-in-part of application No. 15/968,149, filed on May 1, 2018, now Pat. No. 11,957,837,
(Continued)

(51) Int. Cl.
*A61M 16/04* (2006.01)
*A61B 90/00* (2016.01)
(Continued)

(52) U.S. Cl.
CPC ........... *A61M 16/049* (2014.02); *A61B 90/00* (2016.02); *A61F 5/05883* (2013.01);
(Continued)

(58) Field of Classification Search
CPC .............. A61M 16/00; A61M 16/0488; A61M 16/049; A61M 16/0493; A61M 16/0495;
(Continued)

(56) References Cited

U.S. PATENT DOCUMENTS 5,511,544 A * 4/1996 McKenna ......... A61M 16/0045
128/205.13
5,701,885 A * 12/1997 Hale ..................... B63C 11/186
128/207.14
(Continued)

FOREIGN PATENT DOCUMENTS

WO 2019051545 A1 3/2019

OTHER PUBLICATIONS

International Search Report corresponding to International application No. PCT/US2020/28342 mailed Jul. 16, 2020 (12 pages).

*Primary Examiner* — Colin W Stuart
(74) *Attorney, Agent, or Firm* — Maginot, Moore & Beck, LLP

(57) ABSTRACT

A mouthpiece includes a buccal retention feature that produces frictional attachment to the lateral buccal portions (inner cheeks) of the individual user. The mouthpiece includes a U-shaped body sized and shaped to conform to the outer face of the dental arch. The retention feature includes bulbous protrusions that project laterally outward from the body to engage the cheek. The mouthpiece, and particularly the buccal retention feature, has a width that is large enough to prevent dislodgment or removal of the device from the mouth, taking advantage of the decrease in the intercommissural distance as the mouth is opened to attempt to remove the device. The device further includes a duct portion extending forward, outside the mouth, from the body, to permit normal respiration through the duct portion. The duct portion can be configured to connect to other devices, including but not limited to, devices for rebreathing, suctioning, feeding or delivering medicaments.

19 Claims, 16 Drawing Sheets

Related U.S. Application Data which is a continuation-in-part of application No. 14/620,369, filed on Feb. 12, 2015, now Pat. No. 9,987,020, which is a continuation of application No. 12/807,677, filed on Sep. 10, 2010, now Pat. No. 8,985,120.

(60) Provisional application No. 62/834,068, filed on Apr. 15, 2019, provisional application No. 61/260,313, filed on Nov. 11, 2009, provisional application No. 61/241,625, filed on Sep. 11, 2009.

(51) Int. Cl.
| | | |
|---|---|---|
| *A61F 5/058* | (2006.01) | |
| *A61F 5/56* | (2006.01) | |
| *A61M 16/00* | (2006.01) | |
| *A61K 31/07* | (2006.01) | |

(52) U.S. Cl.
CPC ......... *A61F 5/566* (2013.01); *A61M 16/0045* (2013.01); *A61K 31/07* (2013.01)

(58) Field of Classification Search
CPC .. A61M 2210/0625; A61M 2210/0631; A61M 2210/0637; A61M 2210/0643; A62B 9/00; A62B 9/06; A61F 5/56; A61F 5/566; A61F 5/05883; A61F 2005/563; A63B 71/085; A63B 2071/086; A63B 2071/088; A61C 7/08
See application file for complete search history.

(56) References Cited

U.S. PATENT DOCUMENTS

| | | | |
|---|---|---|---|
| 2009/0133696 A1* | 5/2009 | Remmers | A61M 16/0493 128/204.26 |
| 2013/0133648 A1 | 5/2013 | Beach et al. | |
| 2013/0146066 A1 | 6/2013 | Croll | |
| 2013/0167846 A1 | 7/2013 | Hurley | |
| 2014/0166024 A1 | 6/2014 | Davidson et al. | |
| 2014/0276171 A1* | 9/2014 | Hestness | A61B 5/097 600/249 |
| 2015/0190599 A1 | 7/2015 | Colman et al. | |
| 2018/0085247 A1 | 3/2018 | Trainor et al. | |
| 2018/0263841 A1 | 9/2018 | Satake | |
| 2018/0333159 A1 | 11/2018 | Smith | |

* cited by examiner

SELF-RETAINING ORAL DEVICE

REFERENCE TO RELATED APPLICATION

This application claims priority to provisional application No. 62/834,068, entitled "ORAL RETENTION DEVICE", which was filed on Apr. 15, 2019. This application is also a continuation-in-part and claims priority to utility patent application Ser. No. 15/968,149 ("the '149 application"), entitled "METHOD TO REDUCE SLOSH ENERGY ABSORPTION AND ITS DAMAGING EFFECTS THROUGH THE REDUCTION OF INELASTIC COLLISIONS IN AN ORGANISM", which was filed on May 1, 2018, which is a continuation-in-part of U.S. application Ser. No. 14/620,369, filed on Feb. 12, 2015, which is a continuation of U.S. application Ser. No. 12/807,677 (which issued on Mar. 24, 2015 as U.S. Pat. No. 8,985,120), filed Sep. 10, 2010, which claims priority from provisional application No. 61/241,625 filed on Sep. 11, 2009 and provisional application No. 61/260,313 filed on Nov. 11, 2009. The disclosures of all of the above-identified applications are incorporated herein by reference.

BACKGROUND

As discussed in the '149 application, raised inspired carbon-dioxide ($CO_2$), known as hypercapnia, can mitigate traumatic brain injury (TBI) that might otherwise result from impacts and loads experienced by the head of a person. This mitigation occurs through the reduction of macro-slosh inside the cranium, as well as a reduction in micro-slosh inside each individual red blood cell in the brain and reduction in molecular slosh of each individual hemoglobin molecule in the brain's blood supply. The '149 application describes one method to increase pressure within the cranium by temporarily raising the partial pressure of $CO_2$ ($pCO_2$) in the body of the organism by way of altering the fractional percentage of $CO_2$ inspired by the organism. Such a method can maintain the above hypercapnic inspired $CO_2$ levels to exceed ambient levels. In one embodiment disclosed in the '149 application, these levels can be achieved and maintained by an externally imparted respiratory circuit which can modulate the fractional percentage of $CO_2$ inspired by the organism, in particular by rebreathing expired $CO_2$. With each exhaled breath some $CO_2$ is eliminated and with each inhalation, fresh air containing minimal $CO_2$ (presently 0.04%) is inhaled and dilutes the residual equilibrated alveolar $pCO_2$, establishing a new gradient for $CO_2$ to diffuse out of the mixed venous blood into the alveoli. The rate of breathing, or ventilation (VE), usually expressed in L/min, is exactly that required to eliminate the $CO_2$ brought into the lungs and to establish an equilibrium $pET-CO_2$ (end tidal $CO_2$, or $CO_2$ at the end of a breath) and $pA\ CO_2$ (arterial partial $CO_2$) of approximately 35-40 mmHg (in normal humans). The '149 application further describes a customizable re-breathing circuit whose dead space is adjustable based on an individual's weight and estimated tidal volume (i.e., the normal volume of air displaced between inhalation and exhalation), and on the desired or optimized level of hypercapnia (a $pCO_2$ range from 25 to 80 mmHg would be optimum). The re-breathing device deliberately increases the $CO_2$ content of the inhaled air to achieve the benefits of heightened $pCO_2$. The re-breathing circuit thus maintains an estimated, yet elevated, end tidal $pCO_2$ by a device worn by the person that causes a re-breathing of previous inhaled or exhaled breath. The device allows a mixing of inhaled ambient gas and exhaled alveolar gas. The optimal amount of gas re-breathed can be determined by estimating the individual's weight in kilograms and multiplying it by a factor, such as 7, to arrive at an estimated tidal volume in $cm^3$. In one embodiment of the device in the '149 application, a third of this volume is added to the breathing circuit as dead space, which volume determines the predicted level of end tidal $CO_2$ to which the device will equilibrate. In one specific approach, the dead space volume is calibrated to approximately 10%, and even as high as 500%, of the tidal volume of the person wearing the device.

In normal inspiration, a typical person pulls in 500 cc of air, with 21% oxygen ($O_2$), 0.04% carbon-dioxide ($CO_2$) and the balance $N_2$ (nitrogen). In normal expiration, the person pushes 500 cc of air (tidal volume TD), which includes 16% $O_2$ and 4.5% $CO_2$. The devices disclosed in the '149 Application control the mixture of the air that is inhaled by controlling the air that is exhaled. As illustrated in FIG. 12 the device effectively creates three zones of inspiration and expiration of air within an enclosed extended volume. In the first zone nearest the mouthpiece, the $O_2/CO_2$ mixture has its highest $CO_2$ content, while in the third zone at the outlet of the enclosed volume the mixture has its highest oxygen content being closest to the ambient air. The first two zones, Zones 1 and 2, represent, generally, the volume of air that is inhaled and exhaled by the user. The last two zones, Zones 2 and 3, generally represent the volume of air that is fed by ambient air surrounding the device. Although all three zones can be considered "dead space", the middle zone, Zone 2, is the dead space that overlaps the user and the ambient volumes of air. Increasing this intermediate zone increases the $CO_2$ content of the air that is inhaled by the user by, in effect, creating a dead zone for the $CO_2$ exhaled by the user. The $CO_2$ in this dead zone, Zone 2, includes the normal 0.04% $CO_2$ found in the ambient air, with the 3.3-4.5% $CO_2$ typically exhaled by the user. As reflected in the chart in FIG. 12, the content of other gases in the inhaled/exhaled air does not change. Instead, the ratio of $O_2$ to $CO_2$ changes along the mouthpiece and reservoir. Creating and controlling the amounts and relationships of the dead space in the Zones changes the $O_2/CO_2$ ratio by increasing the amount of $CO_2$ retained within the dead space, which in turn replaces the volume of $O_2$ that would ordinarily be inhaled with each breath Certain embodiments of a re-breathing device disclosed in the '149 application can be gripped between the lips and/or teeth of the user are shown in FIGS. 13-21B. The re-breathing device 60 shown in FIGS. 13A-13C includes a chamber 162 that is curved around the jaw of the user. A mouthpiece 164 is integral with the chamber 162 and configured to be gripped by the teeth and/or lips of the user, similar to a typical sports mouth guard. The chamber 162 includes openings 163 at the ends of the curved chamber 162. The chamber is dimensioned to provide a predetermined dead space volume, as discussed above. It is contemplated that the size of the chamber and therefore the size of the apparatus 160 is varied depending on the necessary dead space volume for a particular user.

The re-breathing device 170 shown in FIGS. 14A-14B is similar to the apparatus 160 in that the chamber 172 includes a mouthpiece 175 and defines a fixed volume with an outlet 176 at the opposite ends of the chamber. However, in this embodiment, the internal volume within the chamber 172 can be adjusted by volume pods 174 placed within slots 173 that communicate with the internal volume. The volume pods reduce the internal volume from the maximum total volume of the chamber 172, thereby adjusting the dead space volume.

The re-breathing device 180 shown in FIG. 15 includes an adjustable chamber 182 with outlets 183 at opposite ends. The chamber is defined by an inner wall 185 that includes a mouthpiece as contemplated in the previous embodiments, an outer wall 184 and a bellows structure 186 between the two walls. The bellows can be expanded or contracted to adjust the volume within the chamber 182.

The re-breathing device 190 shown in FIG. 16 includes a chamber 192 with end outlets 193. The outlets are at the ends of adjustable tubes 194 that can slide relative to the chamber.

The re-breathing device 200 of FIG. 17 includes a base chamber 202 that incorporates the mouthpiece 204 and end outlets 203. An additional chamber 206 can be mounted onto the base chamber in a manner that permits fluid or gas communication between the chambers. In one embodiment, the two chambers can be connected with a bayonet mount, similar to the mount used on a traditional camera lens. The additional chamber includes outlets 207 at its ends. The additional chamber 206 may be configured for mounting a further chamber 207, wherein each chamber 206 includes bayonet mounts on the front and back faces of the chamber. Each chamber 203, 206 has a fixed volume, so combining the chambers can achieve a predetermined dead space volume.

An alternative accordion-type embodiment is shown in FIG. 18. A main chamber 212 of the re-breathing device 210 includes the mouthpiece and supports expandable accordion tubes 214, each tube including an outlet 215. The accordion tubes 214 can be extended or contracted to adjust the dead space volume of the apparatus 210.

The re-breathing device 220 shown in FIG. 19 includes a main chamber 221 similar to the main chambers in the prior embodiments. An adjustable wing chamber 222 is provided at each side of the main chamber, with an outlet 223 at the ends of each wing chamber. Each wing chamber 222 is divided into discrete chamber sections 224, with each section separably connected to an adjacent section. The adjacent sections can be connected at score lines 225 or perforations that permit easy separation of an outboard section from an inboard section. Each section can be marked with indicia indicating the total volume of the chamber up to and including the indicated chamber. Removing a particular chamber section 224 reduces the total volume, permitting adjustment of the dead space volume according to the particular user. A similar apparatus 226 is shown in FIGS. 20A-20B in which multiple sections 227 can be separated in a similar manner to alter the dead space volume. It can be appreciated that the apparatuses 220, 226 can be modified so that the segments are separated by cutting the outboard segments away, rather than by separating along score lines or perforations. In this modification, the score lines can be modified to constitute indicator lines for cutting away segments to achieve a pre-defined dead space volume. The apparatus 228 shown in FIG. 21A includes several peel-away segments 229 that can be removed down to a base segment 229a as shown in FIG. 21B. The peel-away segments include tabs 229b that can be grasped to remove a particular segment together with all of the outboard segments to achieve a pre-defined dead space volume as described above.

The outbreak in 2019 of the COVID-19 respiratory virus has severely taxed hospitals and treatment facilities across the globe. The treatment protocol involved the use of ventilators to attempt to stave off the effects of the acute respiratory distress syndrome created by the virus. That treatment protocol involved "permissive hypercapnia", or elevated $CO_2$, as part of the protective lung strategy. Research indicates that the prophylactic use of permissive hypocapnia before the patient's condition deteriorates can slow the clinical course of the COVID-19 virus. According to some research, induced hypercapnic acidosis appears to demonstrate considerable protective effects in several laboratory models of acute lung injury and systemic organ injury. In some instances, introducing more $CO_2$ into the respiration may not result in hypercapnia, but may instead prevent the onset of hypocapnia, or low $CO_2$. Hypocapnia (low $CO_2$) is known to impair alveolar fluid reabsorption. Hypocapnia has been associated with adverse outcomes in mechanically ventilated patients with acute lung injury. In either case, increasing the $CO_2$ respiratory intake can slow the progression of the COVID-19 disease, which not only gives the patient's body more time to combat the virus, it also reduces the likelihood that the patient will require a ventilator. Further, hypercapnia itself may alter the micro-environment of the COVID virus inhibiting the attachment of the virus to human cells or reducing infectivity.

The re-breathing devices described above can be especially valuable in reducing the impact of COVID-19 on the healthcare system. The breathing devices can be adjusted to produce an optimal partial $CO_2$ pressure ($PaCO_2$), which is believed to be in the range of 50-60 mmHG. Levels of fractional inspired $CO_2$ ($FiCO_2$) of 1-5% are also believed to increase resistance to the effects of the COVID-19 virus. The devices can be easily worn by a person for a prescribed time and at prescribed intervals. Moreover, since the person's nostrils are always open there is no risk of $CO_2$ overdose.

As with any medical treatment, patient compliance is a recurring problem. The prophylactic effect of the re-breathing devices disclosed in the '149 application requires adherence to the recommended treatment schedule. One problem with "mouthpiece" type devices is retention, particularly when the person is not deliberately attending to the device, such while sleeping. The typical mouthpiece-type device relies on "bite blocks" onto which the person bites to hold the device in place. Of course, the device only stays in place as long as the person continues to bite down on the bite blocks. Another example is certain oral appliances for addressing sleep apnea that shift the lower jaw forward to open the airway. The user often finds the device on the bed or floor in the morning. Infant pacifiers are notoriously only held in the infant's mouth for 14 minutes on average. Another issue associated with long-term usage of mouthpiece-type devices is the potential for damage to dentition. This issue may not be significant for the limited usage of a re-breathing device, but there is still some potential for damage.

Consequently, there is a need for an oral device, and particularly for a re-breathing device, that can be retained in the person's mouth and that is not susceptible to accidental dislodgement and removal.

SUMMARY OF THE DISCLOSURE

A mouthpiece is provided that includes a buccal retention feature that produces frictional attachment to the lateral buccal portions (inner cheeks) of the individual user. The mouthpiece includes a U-shaped body sized and is shaped to conform to the outer face of the dental arch. The retention feature includes bulbous protrusions that project laterally outward from the body to engage the cheek. The mouthpiece, and particularly the buccal retention feature, has a width that is large enough to prevent dislodgment or removal of the device from the mouth, taking advantage of the decrease in the intercommissural distance as the mouth is opened to attempt to remove the device. The device is configured to be easily manually manipulated to effect insertion and removal of the device. The device includes channels that allow free flow of saliva within the mouth. The device further includes a duct portion extending forward, outside the mouth, from the body, to permit normal respiration through the duct portion when the device is in the person's mouth. The duct portion is configured to connect to a separate device, such as a rebreathing device that creates a dead zone for $CO_2$ exhaled by the person that can be subsequently inhaled to increase the partial $CO_2$ pressure in the person's blood. The mouthpiece may also provide connection to other medicaments or gases for delivery, or provide access to the oral cavity for liquid or gaseous removal.

DETAILED DESCRIPTION

Figure 1:
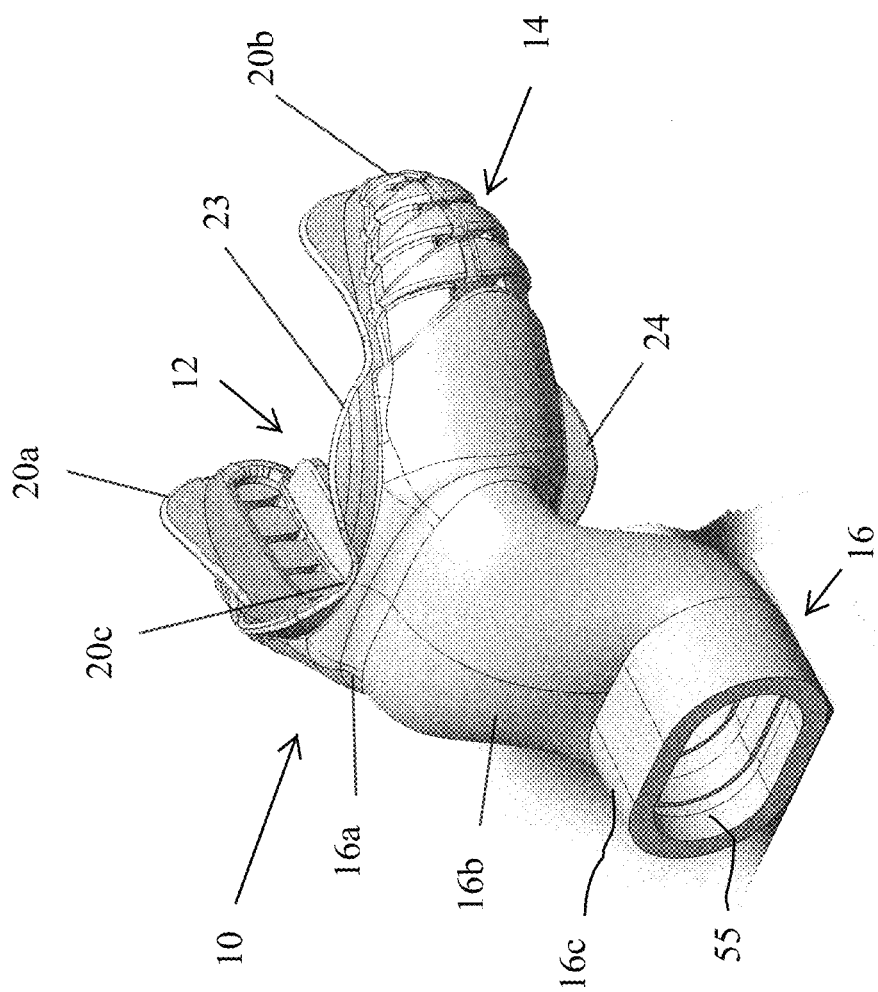
FIG. 1 is a front perspective view of a mouthpiece according to one embodiment of the present disclosure.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles disclosed herein as would normally occur to one skilled in the art to which this disclosure pertains.

A mouthpiece device 10 shown in FIGS. 1-7 utilizes an oral retention mechanism referred to herein as "buccal retention". The device includes a tooth engagement portion 12 that can rest on or against the teeth of the person and a buccal retention portion 14 that is configured to be "gripped" by the cheeks of the individual, with both retention mechanisms being explained in more detail herein. The device includes a duct portion 16 that opens into the mouth cavity to allow the person to breathe through the device.

The device 10 includes a U-shaped body 20 that is sized to fit outside the teeth or on the outer surface of the dental arch of the person. The tooth engagement portion, buccal retention portion and duct portion are all preferably integral and in one piece with the body 20. The body includes a pair of arms 20a, 20b that are situated at the lateral sides of the dental arch, joined by a center section 20c disposed at the front of the dental arch when the device is in the person's mouth. The body 20 includes an interior surface 21 that is adapted to bear against the outer face of the gums and the dental arch, or teeth, of the person. It can be appreciated that the size of the body 20 is determined by the size of the mouth of the person so that the device 10 can be comfortably placed and retained within the person's mouth. The material of the device 10 is also adapted for comfort so that the person is not motivated by pain or discomfort to remove the device. Thus, in one embodiment the device 10 is formed from a suitable polymer, and more specifically silicone with sufficient compliance to be comfortable to the person and sufficient rigidity to hold its shape after length and repeated use.

The body 20 can include upper lobes 23 and lower lobes 24 that are arranged to contact the gums. The upper lobes 23 can be provided with surface features 23a, such as transverse ridges, that contact the inside of the person's upper lip when the device is in place. The lobes 23, 24 are configured to increase the surface area of the device contacting the soft tissue of the person's mouth to thereby spread the pressure across a larger area of tissue, rather than concentrating the retention pressure. The U-shaped body 20 is configured to follow the curvature of the person's mouth between the outer face of the dental arch and the lips and cheeks. This feature allows the lips to apply pressure to the device to produce a seal between the device and the mouth. The "compressed oval" shape of the device further helps to prevent fatigue of the circular muscles of the lips (the orbicularis oris muscles). It is contemplated that the device 10 is formed of a resiliently deformable or pliant material, such as silicone, that allows the device to flex during use, to eliminate the discomfort of a traditional rigid mouthpiece and to help maintain the seal between the device and the mouth. Allowing the device to flex also facilitates insertion and removal of the device in the mouth. In particular, the U-shaped body can be pinched as needed to pass the device into and out of the mouth.

The tooth engagement portion 12 includes a pair of wings 30 that project inward from the interior surface 21 of the body 20. The wings 30 are arranged so that they can contact the first and second molars of the upper and/or lower jaw. It can thus be appreciated that the U-shaped body 20 is sized so that the wings can be positioned at the proper molars. The wings have a length sufficient to be contacted by the majority of the first and second molars. The wings 30 have a transverse or lateral width terminating in a curved inner edge 31 so that the wings do not project inside the teeth into the oral cavity. The wings 30 can serve the primary function of a tooth "guide", rather than the function as a bite-block. In this embodiment, the wings prevent the device 10 from moving too far up or down in the mouth by contacting the upper or lower molars, thereby preventing the device from moving toward the floor or ceiling of the buccal recess and contacting the more sensitive gum line. In this embodiment, the lateral width of the wings 30 need not extend across the width of the molars. In an alternative embodiment, the wings 30 can be sized to be clamped between the teeth of the person.

Figure 2:
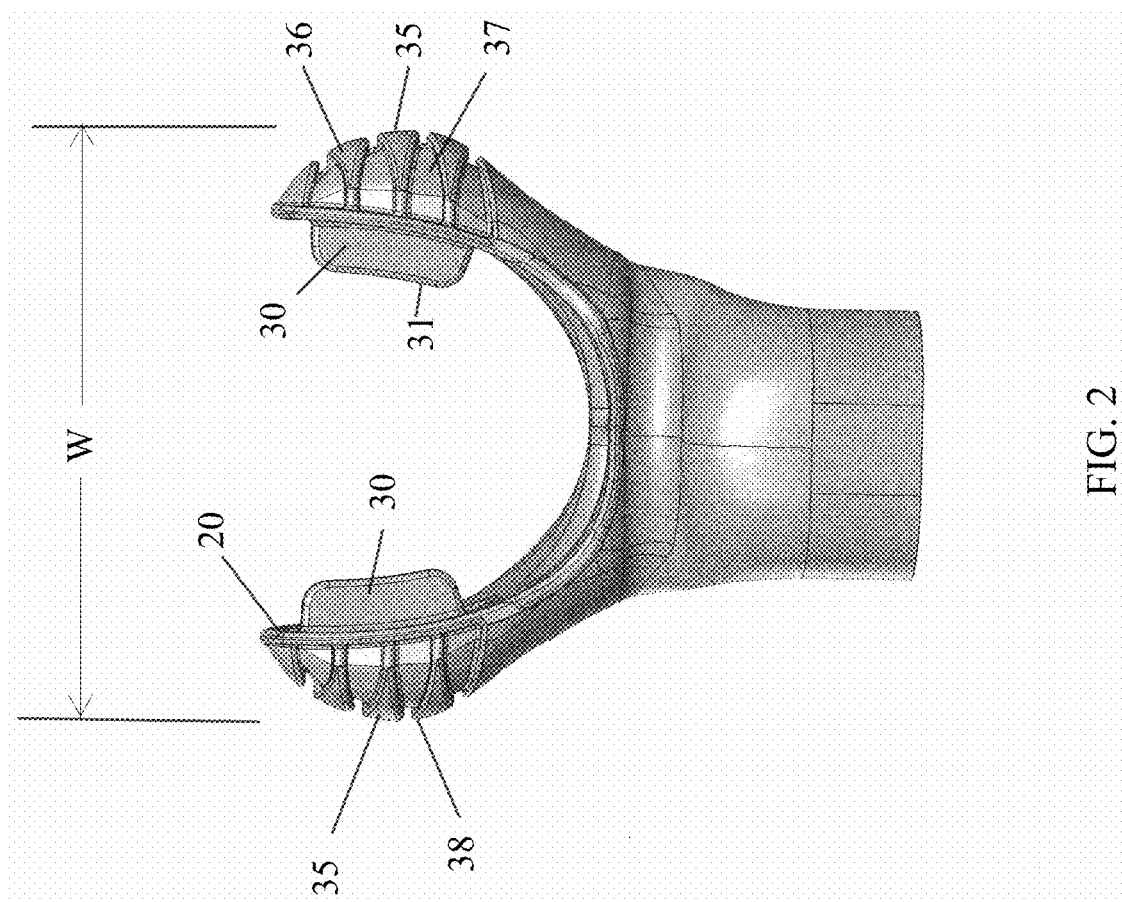
FIG. 2 is a top view of the mouthpiece shown in FIG. 1.
Figure 4:
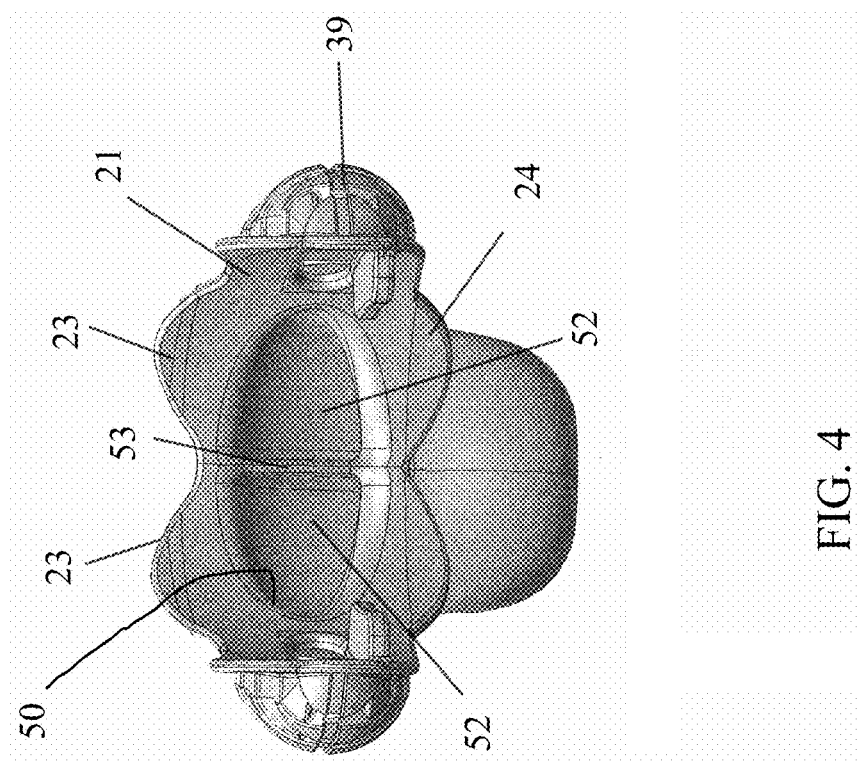
FIG. 4 is a rear view of the mouthpiece shown in FIG. 1.
Figure 11:
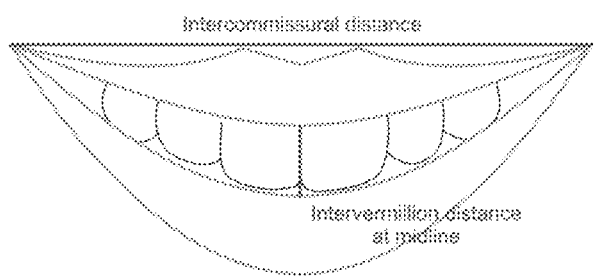
FIG. 11 is a diagram of the dimensions of the mouth of a human.
Figure 12:
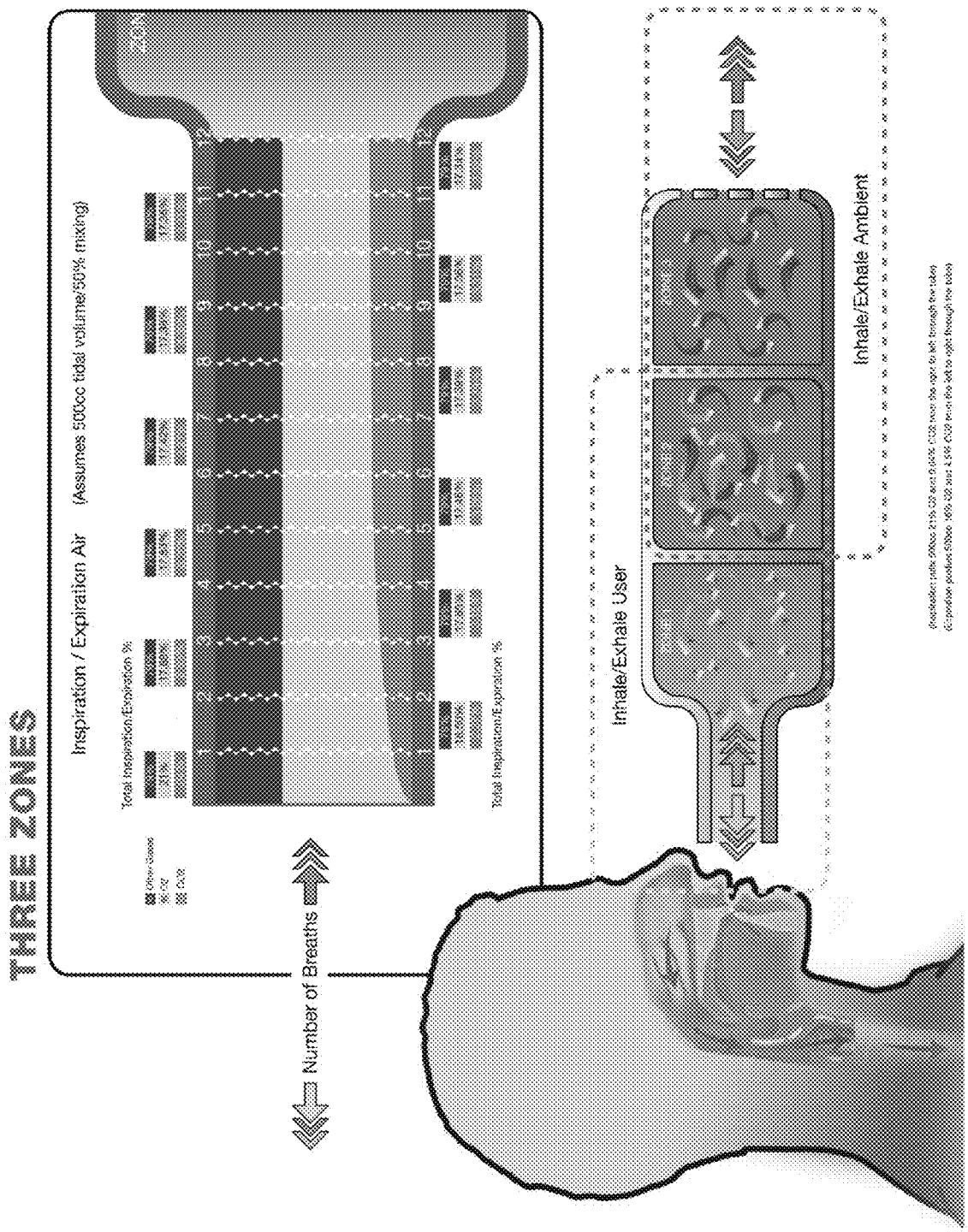
FIG. 12 is a chart showing zones of inspiration and expiration of a human.
Figures 13A, 13B, 13C:
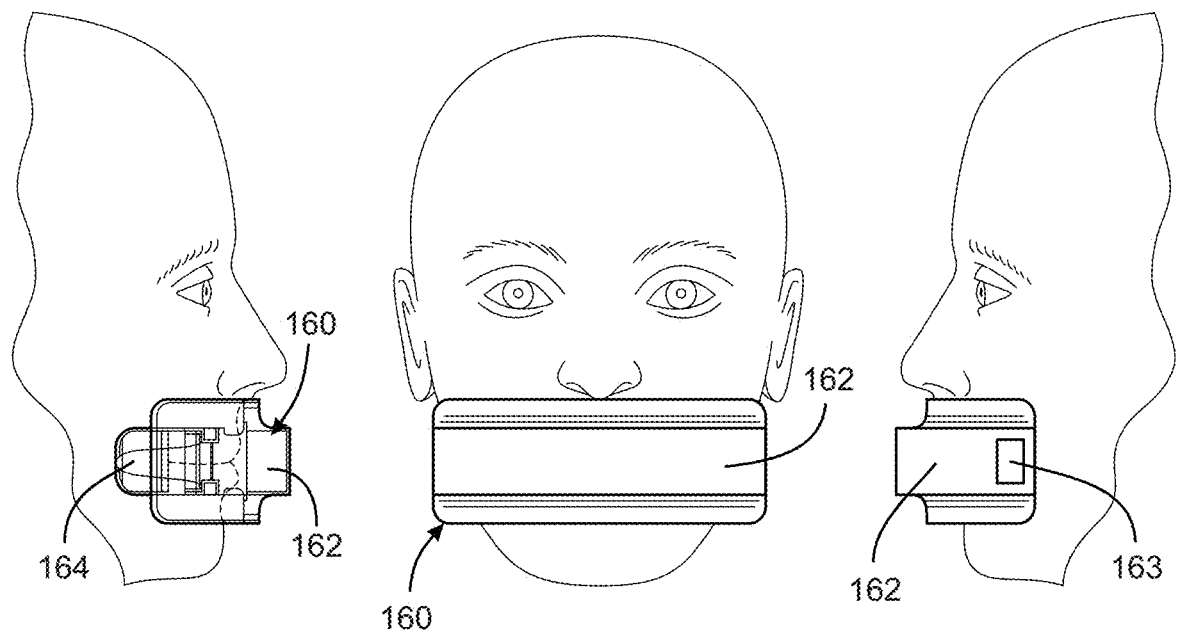
FIGS. 13A-13C are depictions of a mouthpiece-type breathing apparatus according to the present disclosure.
Figures 14A, 14B:
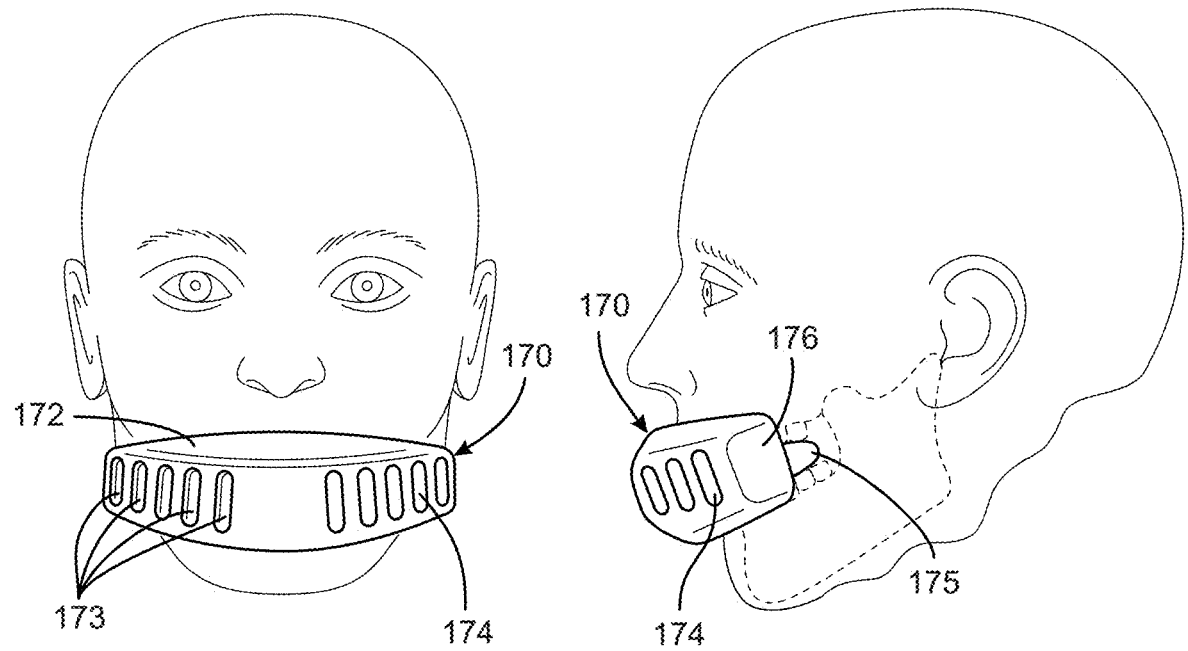
FIGS. 14A-14B are depictions of another mouthpiece-type breathing apparatus according to the present disclosure.
Figure 15:
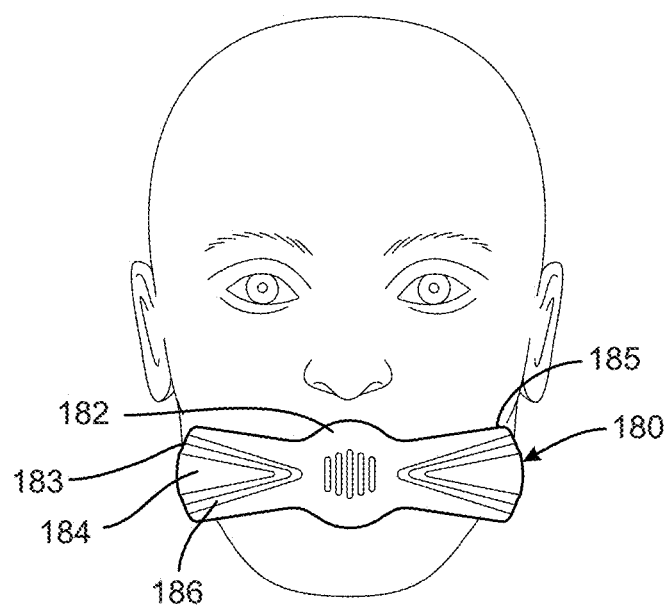
FIG. 15 is a depiction of a mouthpiece-type breathing apparatus having an adjustable dead space volume according to the present disclosure.
Figure 16:
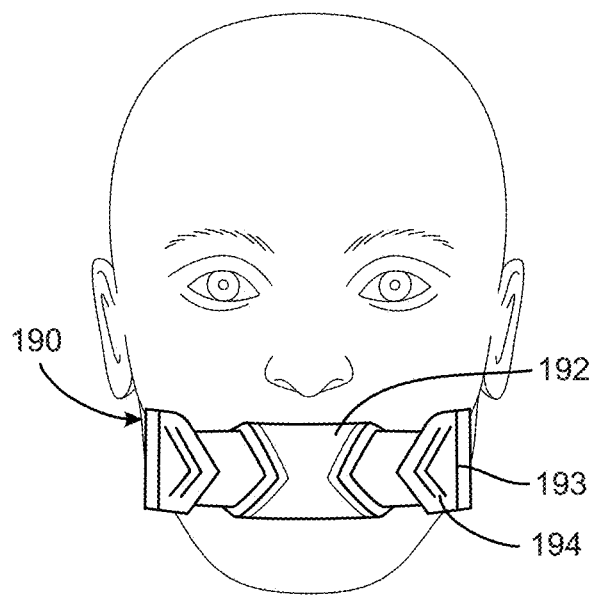
FIG. 16 is a depiction of another mouthpiece-type breathing apparatus having an adjustable dead space volume according to the present disclosure.
Figure 17:
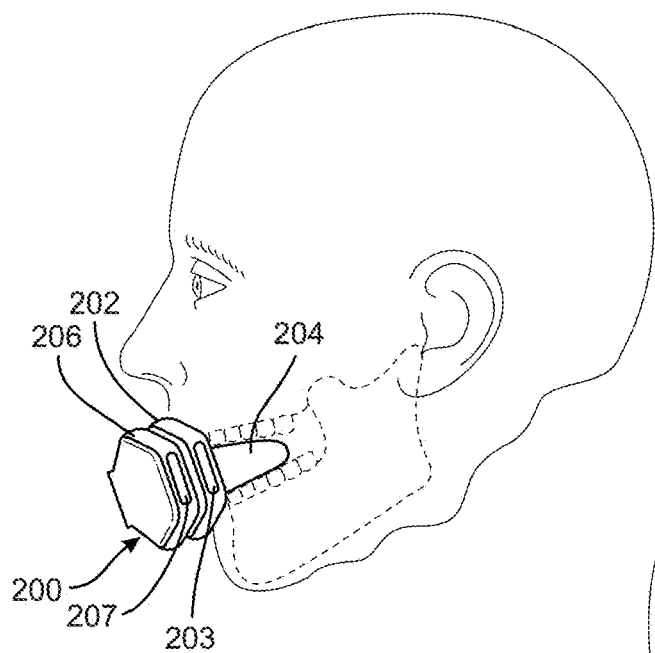
FIG. 17 is a depiction of an alternative mouthpiece-type breathing apparatus having an adjustable dead space volume according to the present disclosure.
Figure 18:
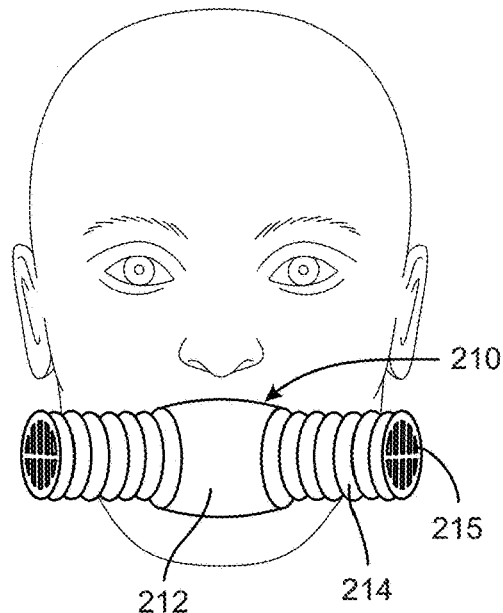
FIG. 18 is a depiction of yet another mouthpiece-type breathing apparatus having an adjustable dead space volume according to the present disclosure.
Figure 19:
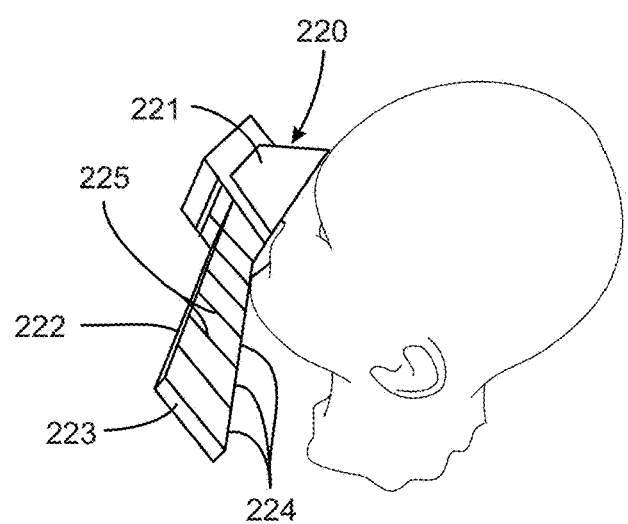
FIG. 19 is a depiction of a further mouthpiece-type breathing apparatus having an adjustable dead space volume according to the present disclosure.
Figure 20B:
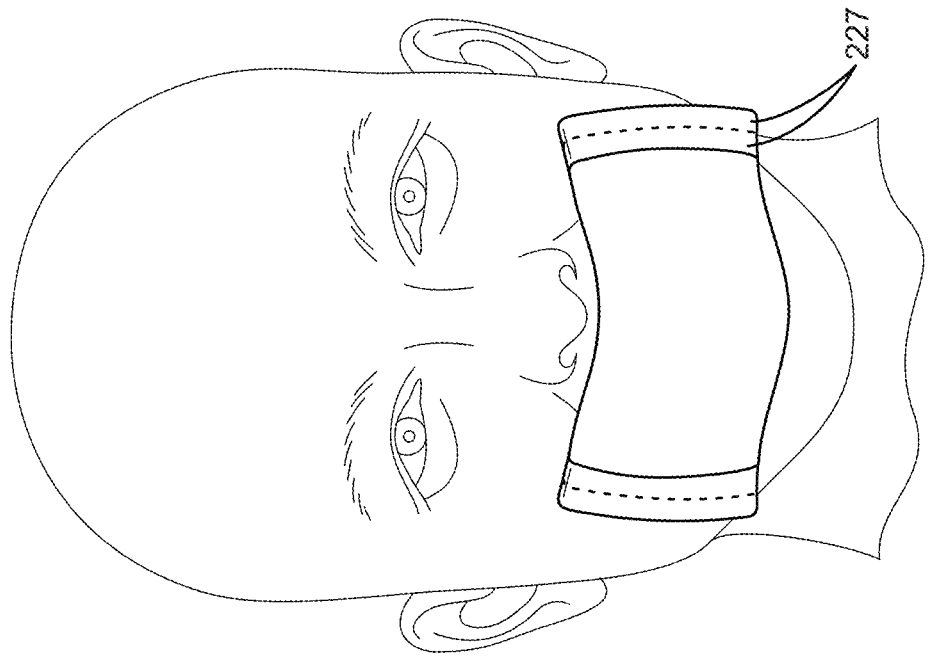
FIGS. 20A-20B are depictions of a further mouthpiece-type breathing apparatus having an adjustable dead space volume according to the present disclosure.
Figure 20A:
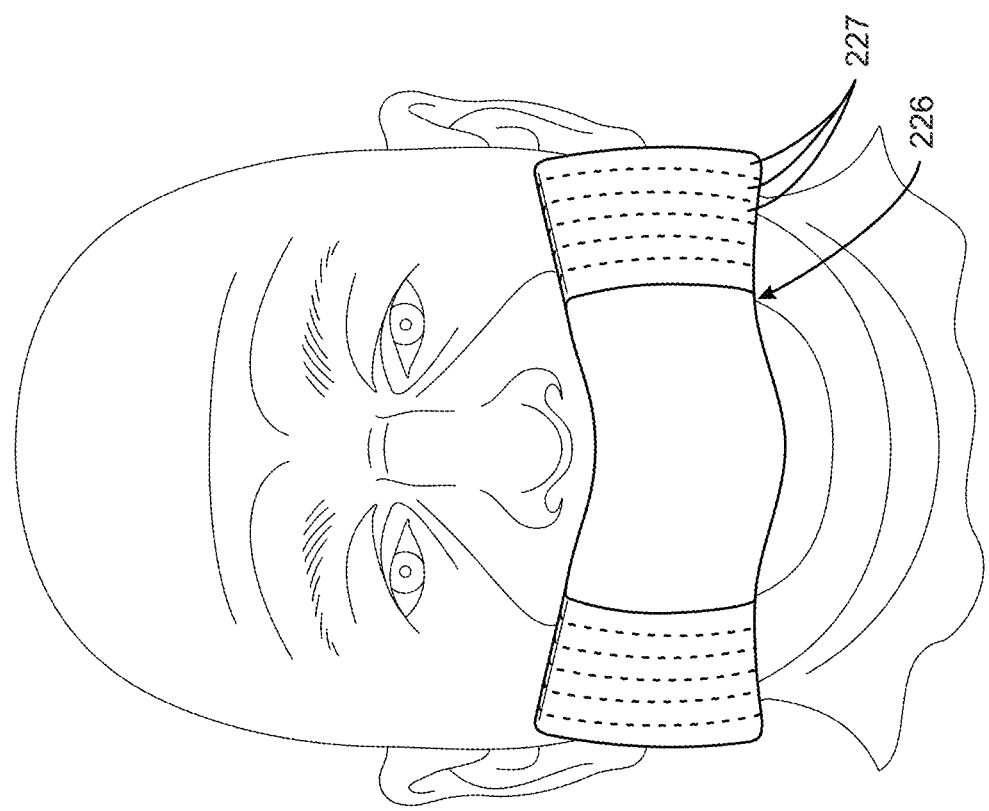
Figure 21B:
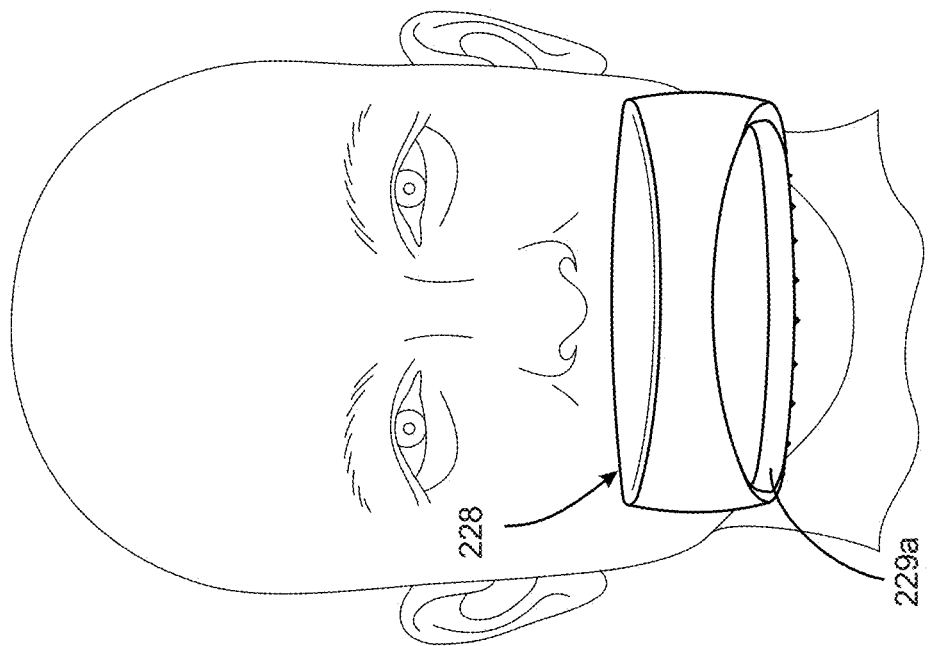
FIG. 21A-21B are depictions of a mouthpiece-type breathing apparatus having an adjustable dead space volume according to the present disclosure.
Figure 21A:
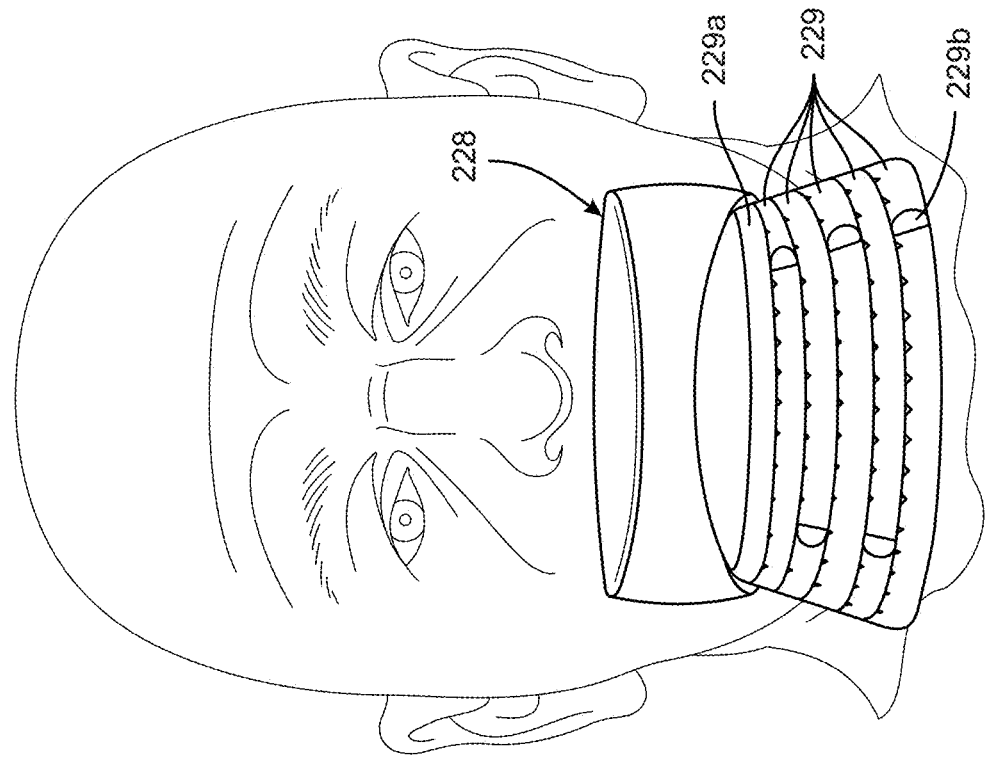

The tooth engagement portion 12 may be optionally eliminated in the device 10, since the primary retention mechanism for the device 10 is the buccal retention portion 14. As best seen in FIGS. 2 and 4 this retention portion 14 includes a bulbous portion or bulbous protrusion 35 defined on the outer face the U-shaped body 20 projecting laterally toward the cheek (buccal region) of the person. The surface area of each bulbous protrusion 35 is large and configured to conform gently with the cheeks while causing a slight protrusion of the cheeks laterally. The large surface area of contact allows a frictional contact with the cheek sufficient to retain the device in place. The bulbous protrusions project laterally outwardly a sufficient amount to take advantage of a physical characteristic of the human mouth. In particular, the intercommissural distance—namely, the distance between the corners of the mouth as shown in FIG. 11—actually gets smaller upon the active opening of the mouth (i.e., increasing the intervermillion distance between the lips as shown in FIG. 11). The overall width W of the device 10 measured from the outer extent of the bulbous protrusions 35 can be approximately equal to the intercommissural distance when the mouth is closed. It can thus be appreciated that when the person opens his/her mouth, the intercommissural distance shortens to less than the width W of the device making accidental expulsion of the device virtually impossible. Even if the person attempts to push the device out with his/her tongue, the device will merely push forward (anteriorly) against the lateral diameter of the corners of the mouth. The cheeks and lips will move forward with the device, but then spring back into the original position because the device is wider than the lateral commissural opening.

The average person can open his/her mouth to a maximum of 35-55 mm (the vertical dimension or the intervermillion distance shown in FIG. 11). The maximum lateral dimension or the intercommissural distance is 38-50 mm when the mouth is closed, depending on the gender, race, age and overall size of the individual. This distance decreases by about 15% to about 32-42 mm when the mouth is wide open, again depending on the individual. In one specific embodiment, the device is provided in at least two sizes—one for smaller adults and one for larger adults. The width W (FIG. 2) of the device is about 57.5 mm or 70 mm, for the smaller and larger individuals, respectively. The height H (FIG. 5) is about 38 mm in both sizes. The bulbous protrusions 35 are sized to project laterally from the outer face of the dental arch from 1 mm to about 30 mm with 15 mm being particularly desirable.

Placement and removal of the device 10 from the person's mouth requires manual manipulation of the device, and particularly pinching the U-shaped body 20 so that the bulbous protrusions 35 can pass through the open mouth. In order to remove the device, it is obviously necessary to open the mouth sufficiently wide to allow passage of the device. Since the intercommissural distance of the person's mouth shortens to less than the width W of the device, it is necessary to reduce the width by pinching the arms 20a, 20b and bulbous protrusions 35 toward each other.

Figure 3:
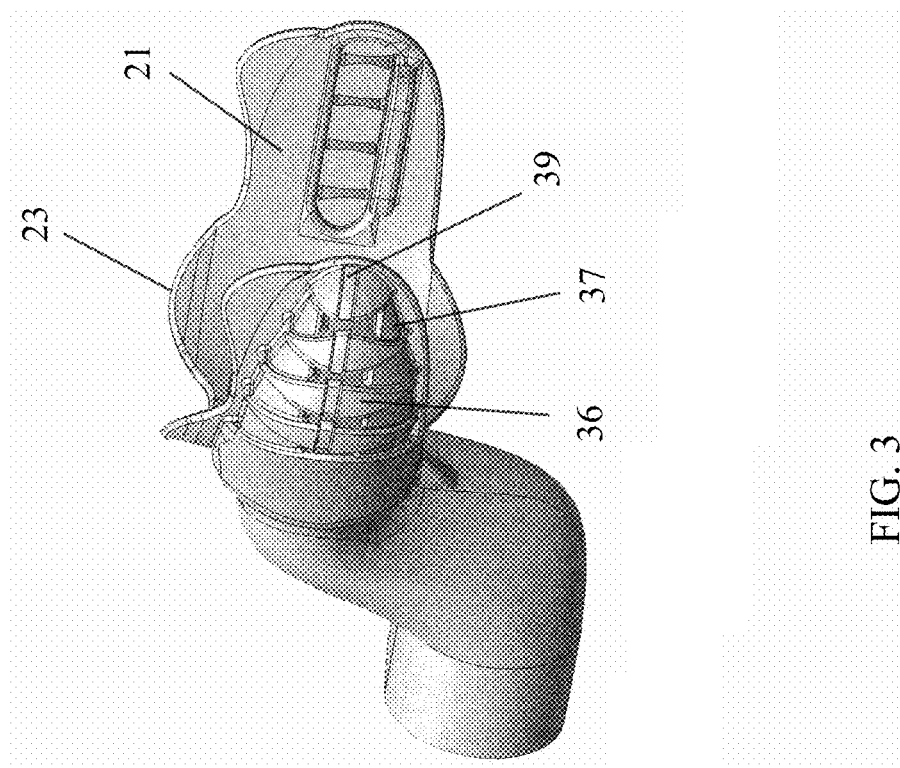
FIG. 3 is a side perspective view of the mouthpiece shown in FIG. 1.

The bulbous protrusions 35 are configured for comfort, frictional engagement and maintaining saliva flow. Accordingly, the portions include treads 36 projecting outward (toward the cheek) from the bulbous surface 37. The treads 36 are spaced apart on the surface 37 in a manner similar to treads on an automobile tire. In the illustrated embodiment, the treads are vertically oriented and longitudinally or fore-aft spaced, relative to the lateral width of the device spanning the protrusions, as best seen in FIGS. 2-3. This tread configuration increases the resistance to dislodgement of the device 10 from the mouth of the person as the soft tissue of the cheek engage the valleys 38 between the treads. The treads 36 can also include a longitudinal or fore-aft channel 39 extending along the length of the bulbous protrusion 35. Like automobile tires, the present disclosure contemplates other tread configurations that are capable of helping to retain the position of the device 10 in the person's mouth, as well as other friction-enhancing surface features, such as ridges or protuberances. It is contemplated that the edges of the treads are formed at a radius to minimize tissue irritation. For that matter, all corners and edges of the device 10 are formed at a radius to minimize irritation and discomfort when the device is held in the mouth for extended periods. The radiused features also help prevent retention of food or dead cells within the mouth.

Figure 5:
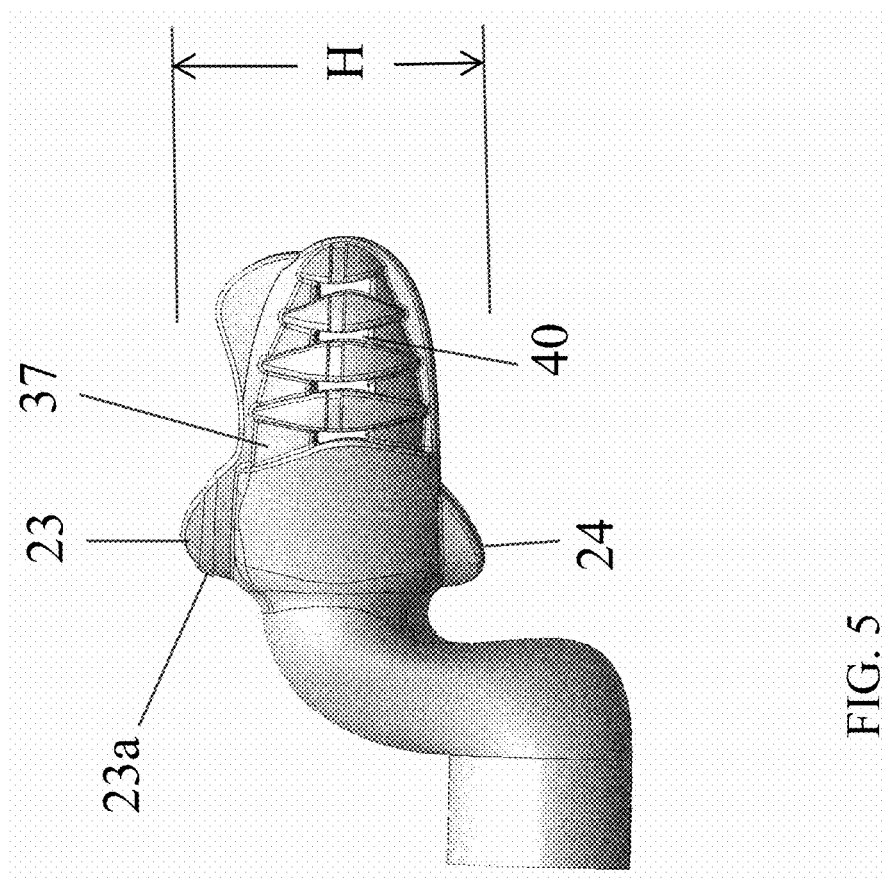
FIG. 5 is a side view of the mouthpiece shown in FIG. 1.
Figure 6:
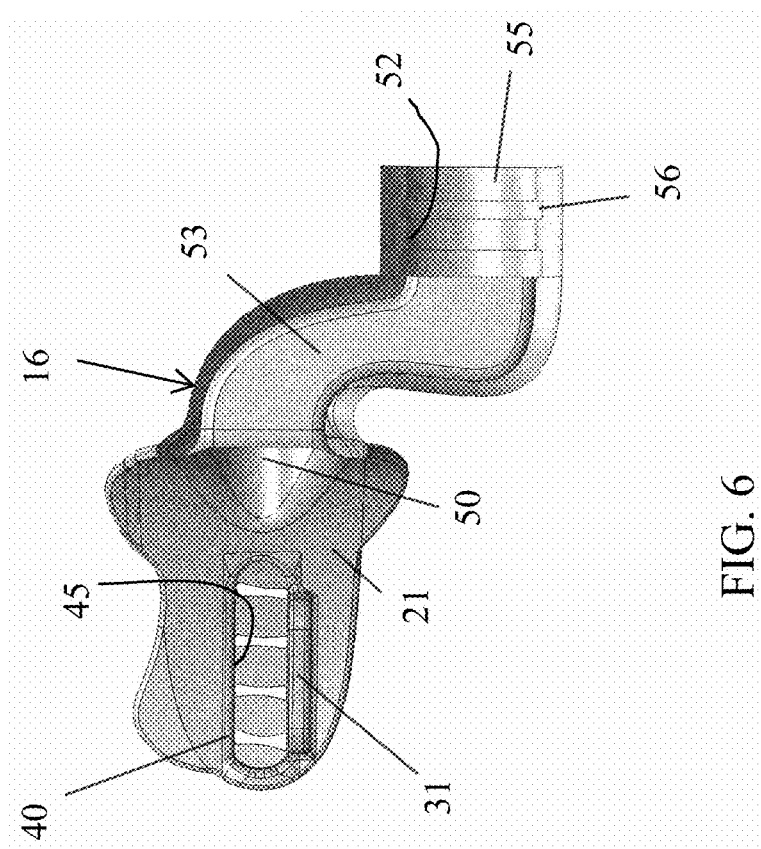
FIG. 6 is a side cross-sectional view of the mouthpiece shown in FIG. 1.
Figure 7:
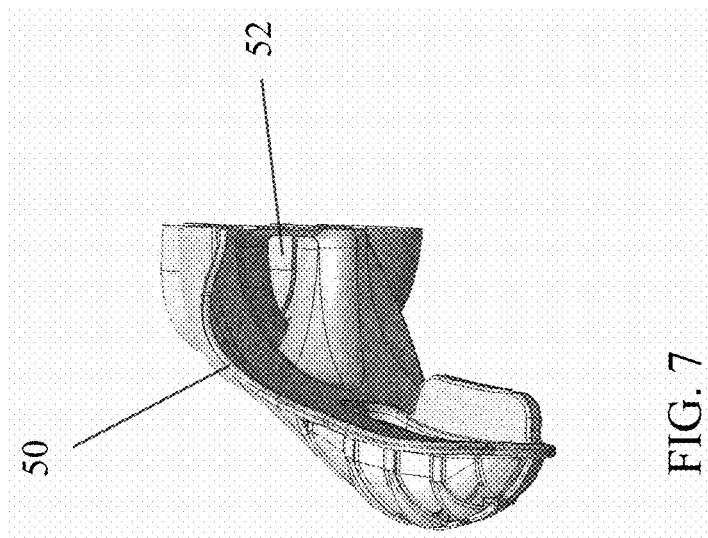
FIG. 7 is a sectioned view of the mouthpiece shown in FIG. 1.

A typical person generates about 1000 ml of saliva a day, which is essential to maintaining good oral health. Consequently, the treads 36, valleys 38 and channel 39 provide passageways for saliva to flow around the bulbous protrusions 35. In addition, openings 40 are provided in the bulbous surface 35, as best seen in FIGS. 5, 6. The openings 40 are aligned with an elongated opening 45 in the inner surface 21 of the U-shaped body 20 to provide a flow path for saliva into the oral cavity. The elongated opening 45 is located immediately above the wings 30 for direct flow into the oral cavity, particularly when the upper and lower molars are parted.

The duct portion 16 provides a passageway for air flow when the device 10 is retained in a person's mouth. The duct begins at an opening 50 defined in the inner surface 21 of the U-shaped body 20. The device 10 is configured so that the opening 50 is centrally oriented in the oral cavity when the device is properly positioned within the mouth. The duct portion 16 can be divided into two channels 52 separated by a septum 53 that extends along the majority of the length of the duct portion as shown in FIG. 6. The duct portion ends in an opening 55 that allows air to flow in and out of the device 10. The opening 55 can include an internal circumferential channel 56 that can be engaged by a separate device to be mounted to the mouthpiece device 10. The duct portion 16 includes an interface section 16a that integrates with the U-shaped body 20, a curved section 16b that curves downward from the mouth, and an outlet section 16c that is in the form of an elongated cylindrical section adapted to mate with auxiliary devices. The septum 53 separates the two channels from the interface section 16a and along the length of the curved section 16b. The curved section 16b orients the opening 55 away from the face of the person and is configured to provide clearance from the chin of the person. In the illustrated embodiment the opening 55, and thus the outlet section 16c, is elongated or oval in shape to accommodate the two channels 52. However, the opening and outlet section can be circular to correspond to standard medical tubing, or can have any other cross-sectional shape depending on the particular device to be integrated with the mouthpiece device 10. The curved section 16b can be modified appropriately to transition from the cross-sectional configuration of the oval opening 52 at the body 20 to the cross-sectional configuration of the outlet section 16c. In that respect, the duct portion 16 can be provided as a separate component from the body 20 and the bite-block and buccal retention portions. In this instance, the opening 52 defined in the body 20 can incorporate a snap-fit of interference-fit feature to engage a similarly configured separate duct portion component. This approach allows a single one-piece component that is disposed within the mouth of the person to attach to several different separate duct portion components.

Figures 8, 9:
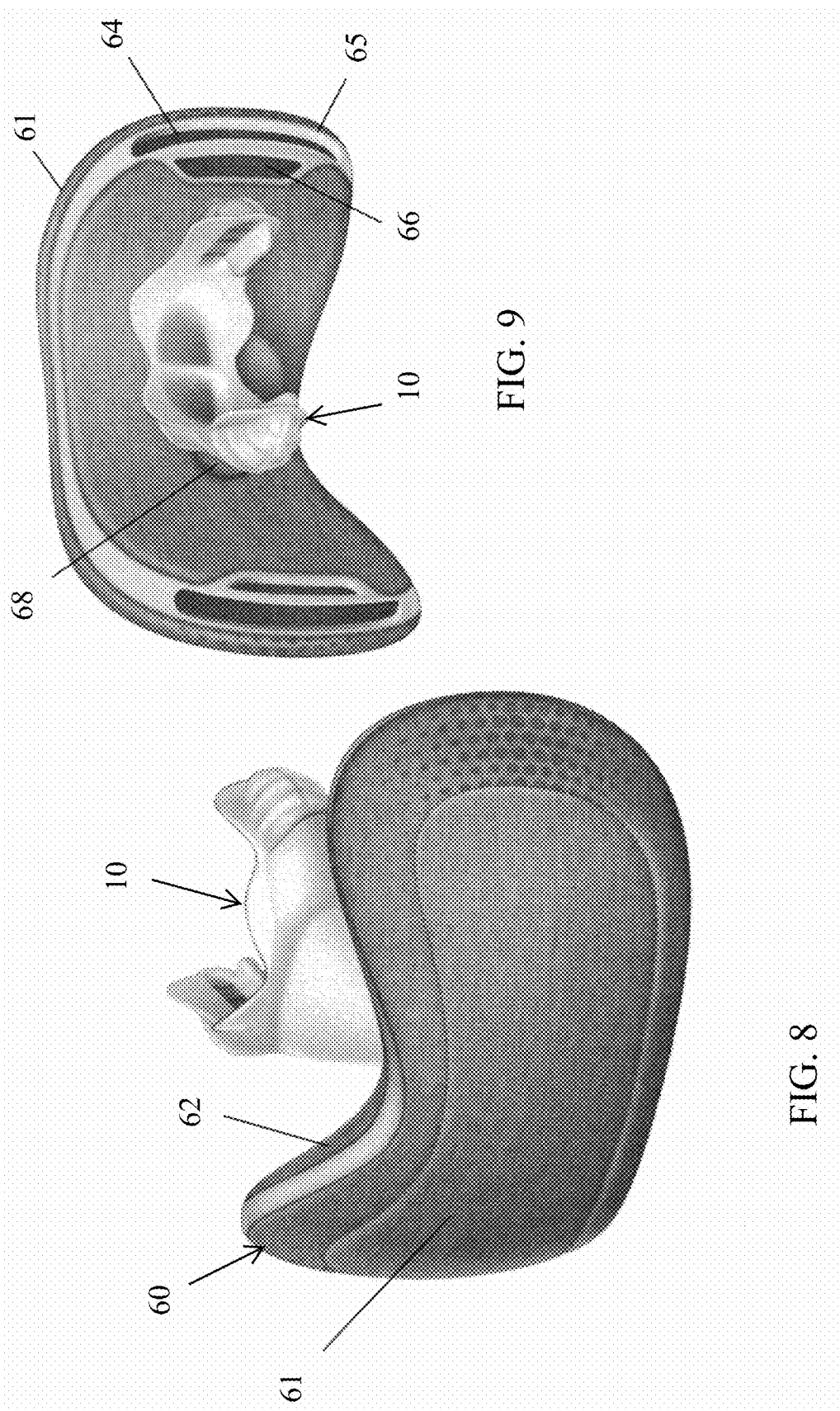
FIG. 8 is a front perspective view of a breathing apparatus including the mouthpiece of FIG. 1 according to one aspect of the present disclosure.
FIG. 9 is a rear perspective view of the breathing apparatus shown in FIG. 8.
Figure 10:
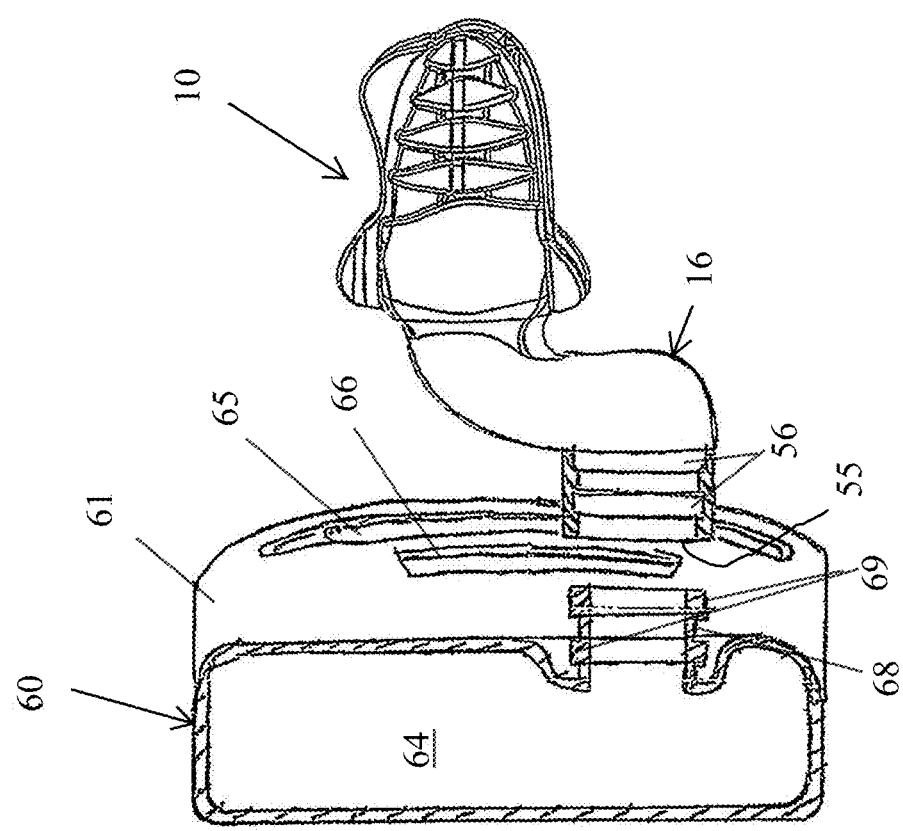
FIG. 10 is a side exploded partial cross-sectional view of the breathing apparatus shown in FIG. 8.

The mouthpiece device 10 is particularly suited for supporting an auxiliary re-breather device, such as the rebreathing device 60 shown in FIGS. 8-10. The rebreathing device includes a body 61 that is contoured to curve around the jaw of the person to minimize the prominence of the device. The body 61 defines an interior chamber 64 with outlet openings 65, 66 at the opposite lateral sides of the device. The body further defines a mating interface 68 that is configured to engage the outlet section 16c of the mouthpiece device 10. The mating interface can be a collar in the body 61 adapted for a press-fit engagement with the outer surface of the outlet section 16c, or can be an elongate cylindrical component with circumferential ridges 69 adapted to fit through the opening 55 and to engage the internal circumferential channels 56 to removably hold the rebreathing device 60 on the mouthpiece 10. The rebreathing device 60 is configured to achieve the rebreathing and $CO_2$ enhancement features of the rebreathing devices disclosed in the '149 application and described above. The rebreathing device 60 can have any of the configurations shown in FIGS. 13-21B that allow calibration of the dead space volume as described above.

The mouthpiece device 10 can also be used with devices other than the rebreathing devices described above. For instance, the outlet section 16c can be coupled to a gas delivery tube. The buccal retention portion of the device holds it in the person's mouth, even if the person is unconscious. The overall configuration of the U-shaped body of the device maintains an air-tight seal during inhalation and exhalation so there is minimal leaking of gas being delivered to the person. The mouthpiece device can also be coupled to tubing of a CPAP machine, eliminating the need to wear a face mask.

The mouthpiece device 10 is preferably integrally formed as one piece, such as in a conventional molding process. The device is formed of a resiliently pliant material that is soft enough to avoid irritation to the soft tissues of the mouth yet rigid enough to maintain its shape when in continuous use. In one embodiment, the device 10 is formed of a thermoformable material, such as the material used in mouth guards, so that the person can heat the device to its moldable temperature and then press the device against the dental arch as it cools. Thus, in certain embodiments the device can be formed of poly(vinyl acetate-ethylene) copolymer or polyurethane.

The mouthpiece device 10 of the present disclosure can be easily retained in a person's mouth without the need to clench the teeth, which can lead to jaw fatigue, temporalmandibular joint (TMJ) dysfunction/pain and other orthodontic problems. The buccal retention portion 14 holds the device in the person's mouth under all circumstances without the need to bite down onto the device. Moreover, the device provides multiple flow paths for saliva originating at the parotid glands in the cheek.

The present disclosure should be considered as illustrative and not restrictive in character. It is understood that only certain embodiments have been presented and that all changes, modifications and further applications that come within the spirit of the disclosure are desired to be protected.

What is claimed is:
1. A mouthpiece comprising:
   a U-shaped body configured to seat against the outer face of the dental arch of a person when the mouthpiece is in the mouth of the person, the U-shaped body including opposite arms defining the U-shape and arranged to be positioned between the dental arch and the lateral buccal portions of the person when the mouthpiece is in the mouth of the person, the body formed of a resiliently pliant material so that the pair of arms can resiliently deflect toward each other;
   an opening defined in said U-shaped body in communication with the oral cavity of the person when the U-shaped body is seated against the outer face of the dental arch;
   a buccal retention portion configured for frictional engagement with the lateral buccal portions (inner cheeks) of the person, the buccal retention portion including a bulbous protrusion on each of the opposite arms, protruding laterally outward from the U-shaped body to frictionally engage the lateral buccal portions of the person to retain the mouthpiece in the mouth of the person, wherein the mouthpiece has a lateral width spanning the bulbous protrusions, the lateral width being greater than the intercommissural distance of the person's mouth when the mouth is at least partially open;
   a duct portion extending from said U-shaped body away from the dental arch when the mouthpiece is in the mouth of the person, the duct portion defining at least one channel in fluid communication with said opening and extending to a second opening outside the mouth of the person when the mouthpiece is in the mouth of the person; and
   at least one pair of lobes extending from said U-shaped body for engagement between the upper and/or lower lips and the corresponding upper and lower gums of the person when the mouthpiece is in the mouth of the person, said at least one pair of lobes including transverse ridges arranged to engage the lip of the person.

2. The mouthpiece of claim 1, wherein the bulbous protrusions include friction enhancing surface features defined on an outer surface of said protrusions, configured and arranged to face the lateral buccal portion of the person when the mouthpiece is in the mouth of the person.

3. The mouthpiece of claim 2, wherein the surface features include treads that are vertically arranged relative to a lateral width of the mouthpiece spanning the bulbous protrusions, and are fore-aft spaced apart in relative to the lateral width of the mouthpiece to define valleys therebetween.

4. The mouthpiece of claim 3, wherein the U-shaped body defines an opening in each of the opposite arms in fluid communication with the valleys defined between the treads.

5. The mouthpiece of claim 3, wherein the bulbous protrusions further define a fore-aft channel through the treads.

6. The mouthpiece of claim 1, wherein said duct portion includes a septum extending along a length of the duct portion to define two adjacent channels.

7. The mouthpiece of claim 1, wherein said duct portion includes a curved portion between said opening and said second opening, said curved portion curved downward from said opening over the chin of the person when the mouthpiece is in the mouth of the person.

8. The mouthpiece of claim 7, wherein said duct portion includes an interface portion between said opening and said curved portion, said interface portion sized to extend the curved portion away from the chin of the person when the mouthpiece is in the mouth of the person.

9. The mouthpiece of claim 1, wherein said U-shaped body, said buccal retention portion and said duct portion are integrally formed as one piece.

10. The mouthpiece of claim 1, wherein said U-shaped body and said buccal retention portion are integrally formed as one piece.

11. The mouthpiece of claim 1, wherein said material is silicone.

12. The mouthpiece of claim 1, further comprising a tooth engagement portion arranged to contact one or more teeth of the person when the mouthpiece is inside the person's mouth.

13. The mouthpiece of claim 12, wherein:
the U-shaped body includes opposite arms arranged to be positioned between the dental arch and the lateral buccal portions of the person; and
the tooth engagement portion includes a wing disposed on each of said opposite arms and projecting laterally inward into the oral cavity of the person when the device is inside the person's mouth, the wing on each of said opposite arms arranged on the U-shaped body to contact at least one of the molars of the person.

14. A breathing apparatus for increasing the partial pressure of carbon-dioxide ($CO_2$) in the blood of a person ($pCO_2$), comprising:
the mouthpiece according to claim 1; and
a rebreathing device mounted to and carried by said mouthpiece including;
a chamber in fluid communication with the opening of said mouthpiece and at least one outlet through which gas flows as the person inhales and exhales when the mouthpiece is in the mouth of the person; and
an enlarged dead space between the opening of said mouthpiece and said at least one outlet, the dead space defining a volume sized to retain a predetermined portion of the $CO_2$ exhaled by the person to be inhaled or re-breathed by the person on the next inhalation.

15. The breathing apparatus of claim 14, wherein the volume of the dead space is sized in relation to the tidal volume of air displaced by the person during inhalation and exhalation to be approximately 10 to 50% of the tidal volume of the person.

16. The breathing apparatus of claim 14, wherein the volume of the dead space is adjustable.

17. An apparatus comprising:
the mouthpiece according to claim 1; and
a tube fluidly connected between said opening of said mouthpiece and an apparatus for one or more of oxygen delivery, gaseous medicament delivery, endotracheal devices and feeding devices.

18. The mouthpiece of claim 1, wherein said at least one pair of lobes are centered relative to a midline of the mouthpiece.

19. The mouthpiece of claim 1, wherein said at least one pair of lobes includes an upper pair of lobes arranged for engagement between the upper lip and upper gum of the person and a lower pair of lobes arranged for engagement between the lower lip and lower gum of the person.

* * * * *